(12) United States Patent
Rittman, III

(10) Patent No.: US 7,853,326 B2
(45) Date of Patent: *Dec. 14, 2010

(54) METHOD AND APPARATUS FOR DIAGNOSING AND TREATING NEURAL DYSFUNCTION

(75) Inventor: William J. Rittman, III, Middleton, MA (US)

(73) Assignee: NeuroTherm, Inc., Wilmington, MA (US)

( * ) Notice: Subject to any disclaimer, the term of this patent is extended or adjusted under 35 U.S.C. 154(b) by 52 days.

This patent is subject to a terminal disclaimer.

(21) Appl. No.: 12/501,074

(22) Filed: Jul. 10, 2009

(65) Prior Publication Data

US 2010/0016926 A1    Jan. 21, 2010

Related U.S. Application Data

(63) Continuation of application No. 11/498,446, filed on Aug. 2, 2006, now Pat. No. 7,574,257.

(60) Provisional application No. 60/704,849, filed on Aug. 2, 2005.

(51) Int. Cl.
*A61N 1/00* (2006.01)
(52) U.S. Cl. .......................................... 607/2
(58) Field of Classification Search ............... 607/2–7; 600/16–18, 508–528; 606/32, 34, 41, 49
See application file for complete search history.

(56) References Cited

U.S. PATENT DOCUMENTS

| | | |
|---|---|---|
| 3,898,991 A | 8/1975 | Ikuno et al. ............ 128/303.14 |
| 4,907,589 A | 3/1990 | Cosman |
| 5,233,515 A | 8/1993 | Cosman |

(Continued)

FOREIGN PATENT DOCUMENTS

EP    1493397    1/2005

(Continued)

OTHER PUBLICATIONS

Examination Report of Jul. 10, 2009, Application No. 06 117 004.9-2305.

(Continued)

*Primary Examiner*—George Manuel
*Assistant Examiner*—Robert N Wieland
(74) *Attorney, Agent, or Firm*—Sunstein Kann Murphy & Timbers LLP

(57) ABSTRACT

A method and apparatus for diagnosing and treating neural dysfunction is disclosed. This device has the capability of delivering the therapeutic electrical energy to more than one treatment electrode simultaneously. In another exemplary embodiment, this device can perform EMG testing both before and after the therapeutic energy has been delivered, to assess whether the target nerve was successfully treated. In another embodiment, the device has the capability to record and store sensory stimulation thresholds both before and after treatment is described, which allows the clinician to accurately determine whether the target nerve has been desensitized. Energy control may achieved by simultaneously comparing the tip temperature of each treatment electrode to a set temperature selected by the operator, and regulating the therapeutic energy output to maintain the set temperature. In another embodiment, EMG, stimulation thresholds, and graphs of temperature versus time can be conveniently displayed on a two-dimensional graphics display.

27 Claims, 7 Drawing Sheets

U.S. PATENT DOCUMENTS

| | | | |
|---|---|---|---|
| 5,370,672 A | 12/1994 | Fowler et al. | |
| 5,433,739 A | 7/1995 | Sluijter et al. | |
| 5,456,682 A | 10/1995 | Edwards et al. | |
| 5,474,558 A | 12/1995 | Neubardt | |
| 5,678,568 A | 10/1997 | Uchikubo et al. | |
| 5,718,701 A | 2/1998 | Shai et al. | |
| 5,782,826 A | 7/1998 | Swanson | |
| 5,820,568 A | 10/1998 | Willis | |
| 5,837,001 A | 11/1998 | Mackey | |
| 5,868,666 A | 2/1999 | Okada et al. | |
| 5,868,737 A | 2/1999 | Taylor et al. | |
| 5,871,481 A | 2/1999 | Kannenberg et al. | |
| 5,951,546 A | 9/1999 | Lorentzen | |
| 5,983,141 A | 11/1999 | Sluijter et al. | |
| 6,006,129 A | 12/1999 | Watson | |
| 6,014,581 A | 1/2000 | Whayne et al. | |
| 6,056,745 A | 5/2000 | Panescu et al. | |
| 6,074,213 A | 6/2000 | Hon | |
| 6,117,127 A | 9/2000 | Helmreich et al. | |
| 6,123,702 A | 9/2000 | Swanson et al. | |
| 6,161,048 A | 12/2000 | Sluijter et al. | |
| 6,212,426 B1 | 4/2001 | Swanson | |
| 6,231,569 B1 | 5/2001 | Bek et al. | |
| 6,246,912 B1 | 6/2001 | Sluijter et al. | |
| 6,251,113 B1 | 6/2001 | Appelbaum et al. | |
| 6,259,952 B1 | 7/2001 | Sluijter et al. | |
| 6,312,426 B1 | 11/2001 | Goldberg et al. | |
| 6,409,722 B1 | 6/2002 | Hoey et al. | |
| 6,416,520 B1 | 7/2002 | Kynast et al. | |
| 6,440,127 B2 | 8/2002 | McGovern et al. | |
| 6,447,505 B2 | 9/2002 | McGovern et al. | |
| 6,451,015 B1 | 9/2002 | Rittman, III et al. | |
| 6,478,793 B1 | 11/2002 | Cosman et al. | |
| 6,506,189 B1 | 1/2003 | Rittman, III et al. | |
| 6,517,534 B1 | 2/2003 | McGovern et al. | |
| 6,530,922 B2 | 3/2003 | Cosman et al. | |
| 6,565,511 B2 | 5/2003 | Panescu et al. | |
| 6,572,551 B1 | 6/2003 | Smith et al. | |
| 6,575,969 B1 | 6/2003 | Rittman, III et al. | |
| 6,692,493 B2 | 2/2004 | McGovern et al. | |
| 6,881,214 B2 | 4/2005 | Cosman et al. | |
| 6,918,771 B2 | 7/2005 | Arington et al. | |
| 7,169,143 B2 | 1/2007 | Eggers et al. | |
| 7,270,659 B2 | 9/2007 | Ricart et al. | |
| 7,282,049 B2 | 10/2007 | Orszulak et al. | 606/34 |
| 7,331,956 B2 * | 2/2008 | Hovda et al. | 606/32 |
| 7,344,533 B2 | 3/2008 | Pearson et al. | 606/41 |
| 7,574,257 B2 * | 8/2009 | Rittman, III | 607/2 |
| 2003/0032951 A1 | 2/2003 | Rittman et al. | |
| 2005/0113703 A1 * | 5/2005 | Farringdon et al. | 600/509 |
| 2005/0113730 A1 | 5/2005 | Runeman et al. | |
| 2005/0277918 A1 | 12/2005 | Shah et al. | |
| 2006/0085054 A1 | 4/2006 | Zikorus et al. | |
| 2006/0095103 A1 | 5/2006 | Eggers et al. | |
| 2006/0282139 A1 | 12/2006 | Weintraub | |
| 2006/0289528 A1 | 12/2006 | Chiu et al. | |
| 2007/0043405 A1 | 2/2007 | Rittman, III | |
| 2007/0100278 A1 | 5/2007 | Frei et al. | |
| 2007/0118109 A1 | 5/2007 | Baker et al. | |
| 2007/0142873 A1 | 6/2007 | Esteller et al. | |
| 2007/0142875 A1 | 6/2007 | Shalev et al. | |
| 2007/0250119 A1 | 10/2007 | Tyler et al. | |
| 2008/0004615 A1 | 1/2008 | Woloszko et al. | |
| 2008/0009847 A1 | 1/2008 | Ricart et al. | |
| 2008/0046012 A1 | 2/2008 | Covalin et al. | |
| 2008/0287944 A1 * | 11/2008 | Pearson et al. | 606/41 |

FOREIGN PATENT DOCUMENTS

| | | |
|---|---|---|
| WO | WO 85/01213 | 3/1985 |
| WO | WO 94/00188 | 1/1994 |
| WO | WO 97/13550 | 4/1997 |
| WO | WO 97/49453 | 12/1997 |
| WO | WO 01/12089 | 2/2001 |
| WO | WO 2004/067085 A1 | 8/2004 |
| WO | WO 2006/092021 | 9/2006 |
| WO | WO 2006/099462 | 9/2006 |
| WO | WO 2006/119467 | 11/2006 |
| WO | WO 2006/134598 | 12/2006 |

OTHER PUBLICATIONS

Reply to Examination Report, Application No.: 006 117 004.9; filed Jan. 13, 2010.

Communication Under Rule 71(3) EPC; Application No.: 06 117 004.9-2305; Feb. 18, 2010.

Cosman, et al,; Method of Making Nervous System Lesions, in Wilkins RH, Rengachary SS (eds); (1984); Neurosurgery, vol. III; pp. 2490-2498.

Cosman, et al.; Theoretical Aspects of Radiofrequency Lesions and the Dorsal Root Entry Zone; (1984); Neurosurgery; 15: pp. 945-950.

Salkoff; Temperature-induced seizure and frequency-dependent neuromuscular block in a ts mutant drosophilia; (1978); Nature (UK); 273, No. 5658: pp. 156-158.

Guttman, et al.; Squid axon membrane response to white noise stimulation; (1974); Biophys. J. (USA); 14, No. 12: pp. 941-955.

European Search Report and Opinion for European Patent Application No. 06117344.9, mailed Feb. 4, 2008.

European Search Report and Opinion for European Patent Application No. 06117344.9, mailed Oct. 21, 2008.

Examination Report for European Patent Application No. 06117004.9, mailed Aug. 4, 2008.

Examination Report for European Patent Application No. 06117004.9, mailed Jul. 24, 2007.

European Search Report and Opinion for European Patent Application No. 06117004.9, mailed Sep. 22, 2006.

Official Action for U.S. Appl. No. 11/498,446, mailed Nov. 26, 2008.
Official Action for U.S. Appl. No. 11/498,446, mailed Feb. 26, 2009.
Notice of Allowance for U.S. Appl. No. 11/498,446, mailed Jun. 12, 2009.

Official Action for U.S. Appl. No. 11/506,748, mailed Aug. 20, 2009.

* cited by examiner

METHOD AND APPARATUS FOR DIAGNOSING AND TREATING NEURAL DYSFUNCTION

CROSS REFERENCE TO RELATED APPLICATIONS

This application is a continuation of U.S. patent application Ser. No. 11/498,446 filed on Aug. 2, 2006, entitled "Method and Apparatus for Diagnosis and Treating Neural Dysfunction", which issued as U.S. Pat. No. 7,574,257 on Aug. 11, 2009, and which claims priority to U.S. Provisional Patent Application No. 60/704,849, filed on Aug. 2, 2005, the entire disclosures of which are hereby incorporated herein by reference.

FIELD

The presently described system relates generally to the advancement of medical technology, processes, and systems for the treatment of pain, neurological disorders, and other clinical maladies related to neural dysfunction. More specifically, the present disclosure is directed at a system for producing therapeutic lesions or tissue alterations by means of a high frequency generator connected to a patient via more than one electrode. In below-described exemplary embodiments, therapeutic energy is delivered and regulated simultaneously. Various specific exemplary embodiments of this device accommodate specific exemplary clinical applications and designs.

BACKGROUND

The general use of radiofrequency and high frequency generator systems which deliver electrical output to electrodes that are connected to a patient's body is known in the clinical literature and art.

By reference, an example of radiofrequency heat lesioning generators used in clinical practice for the treatment of neural disorders is the Radionics RFG-3C+ (Burlington Mass.).

This device is capable of delivering high frequency energy to patient tissue via an adapted electrode, and associated ground or reference electrode. This device is also capable of delivering low frequency stimulation pulses that are used to accurately localize the electrode placement before treatment.

Parameters that may be measured by these devices include impedance, HF voltage, HF current, HF power, and electrode tip temperature. Parameters that may be set by the user include time of energy delivery, desired electrode temperature, stimulation frequencies and durations, and level of stimulation output. In general, electrode temperature is a parameter that may be controlled by the regulation of high frequency output power.

These devices have various user interfaces that allow the selection of one or more of these treatment parameters, as well as various methods to display the parameters mentioned above.

In one application of these devices, a patient complains of back pain, or some other pain of nocioceptive or neuropathic origin. A doctor then performs diagnostic blocks with local anesthetic by injecting the anesthetic into the areas that is suspected of generating the pain. If the patient receives temporary relief from these injections the doctor concludes that the pain generators were in the location where he made these injections. Unfortunately, the origin of pain is poorly understood; perceived pain at a certain level in the back, for instance, can actually be created from many different and multiple sources.

Once a location has been identified, the clinician will decide to deliver high frequency energy to this location to permanently destroy the pain generator. A ground or reference plate will be placed on the patient's thigh to provide a return path for the high frequency energy. An insulated electrode with a small un-insulated tip will be placed at the expected target. Stimulation pulses will be delivered at a sensory frequency (typically 50 Hz), and a stimulation voltage will be placed on the electrode. The clinician is looking for a very low threshold of response from the patient (e.g., less than 0.5 V) to ensure that the electrode is close to the sensory nerves. They will then perform a stimulation test at a muscle motor frequency (e.g., 2 Hz), and increase the stimulation voltage output to 2 v. In this instance, they are looking for no motor response in the patient's extremities as this would indicate the electrode was too close to the motor nerves. Treatment in this area could cause paralysis. Upon successful completion of these tests, high frequency energy is typically delivered for one or more minutes, while maintaining an electrode tip temperature between 70 and 90 degrees. Alternatively, high frequency energy may be delivered for one or more minutes, but in a pulsed mode where the high frequency energy is on for a short period of time and off for a long period of time, thus not producing any appreciable heating (reference is made to commonly assigned U.S. Pat. No. 6,161,048, the entire contents of which are specifically incorporated by reference herein).

Although these treatments are successful, they have several drawbacks. In practice, most patients need treatments at several different nerve locations. This requires placing the electrode, performing the stimulation, and delivering the energy at each location and then repeating the process, thus causing a great deal of wasted time, and patient discomfort, while waiting for the energy to be delivered. Another drawback is that in spite of successful stimulation testing, the target nerve is often not destroyed resulting in no decrease of pain. The clinician is left to determine whether the target nerve has been missed, or whether the pain generator is located else where in the body.

SUMMARY

The above-described and other disadvantages of the art are overcome and alleviated by the present method and system for taking the energy output from a high frequency generator module and delivering this energy simultaneously to more than one treatment electrode. In one exemplary embodiment, the energy is regulated by a feedback mechanism such that each electrode's tip temperature is maintained to a level set by the user. This greatly reduces treatment time, providing the patient with a shorter period of discomfort as well as not wasting valuable procedure room time.

In additional exemplary embodiments, EMG measurements are displayed to allow the clinician to determine whether the target nerve has been destroyed, as well as the display of pre-treatment and post-treatment sensory stimulation thresholds to measure the degree of desensitation of the target nerve. Regarding the EMG measurements, this allows the clinician to determine whether the target nerve has been successfully treated; if it has been, then other pain generation sources need to be investigated. The capability of being able to compare pre-treatment and post-treatment sensory stimulation thresholds gives the clinician an immediate look at the immediate desensitation of the target nerve.

In accordance with one exemplary embodiment, the device receives input from a module capable of delivering both high frequency energy as well as low frequency stimulation pulses, such as between 1 and 100 Hz. The device is, in turn, connected to greater than one treatment electrode. These electrodes have temperature sensors attached to their tips, which reports the tip temperature of each electrode to the device. The device has a user interface which allows the output from the said module to be independently connected to each said electrode and also a means which connects all the electrodes simultaneously to the output of the said module. In this way, the low frequency stimulation output can be independently connected to each of the patient electrodes, and then the said electrodes can be connected simultaneously to the high frequency power source, thus permitting temperature regulation of the three electrodes simultaneously. This allows both sensory and motor stimulation testing, as well as impedance monitoring to be performed on each electrode one at a time. When the therapeutic energy is desired to be delivered, the user interface allows a means which connects all electrodes together simultaneously. The device then receives the tip temperature from each of the multiple electrodes, as well as a set temperature for each electrode that is chosen by the user. The device continually compares each of the temperatures from the electrodes to the set temperature. If the electrode tip temperature ever exceeds the set temperature, the high frequency energy is disconnected from that electrode. Similarly, if the electrode tip temperature is ever less than the set temperature, the high frequency energy is either left connected or reconnected to that electrode.

Another exemplary embodiment of this invention incorporates a graphic display, which allows EMG signals to be recorded to and displayed. An additional provision allows for a speaker and/or a headphone output so that the EMG signals can also be audibly detected and analyzed.

It should be noted that the present system and method can be incorporated into high frequency power source, or can be a stand-alone peripheral device that connects in-between the high frequency power source and the electrodes.

For at least the reasons described above, this method and invention provides practical and clinical advantages in the treatment of pain. Additional advantages will become apparent in the detailed descriptions that follow.

The above discussed and other features and advantages of the present system will be appreciated and understood by those skilled in the art from the following detailed description and drawings.

BRIEF DESCRIPTION OF THE DRAWINGS

Referring now to the figures, which are exemplary embodiments and wherein the like elements are numbered alike.

DETAILED DESCRIPTION

Figure 1:
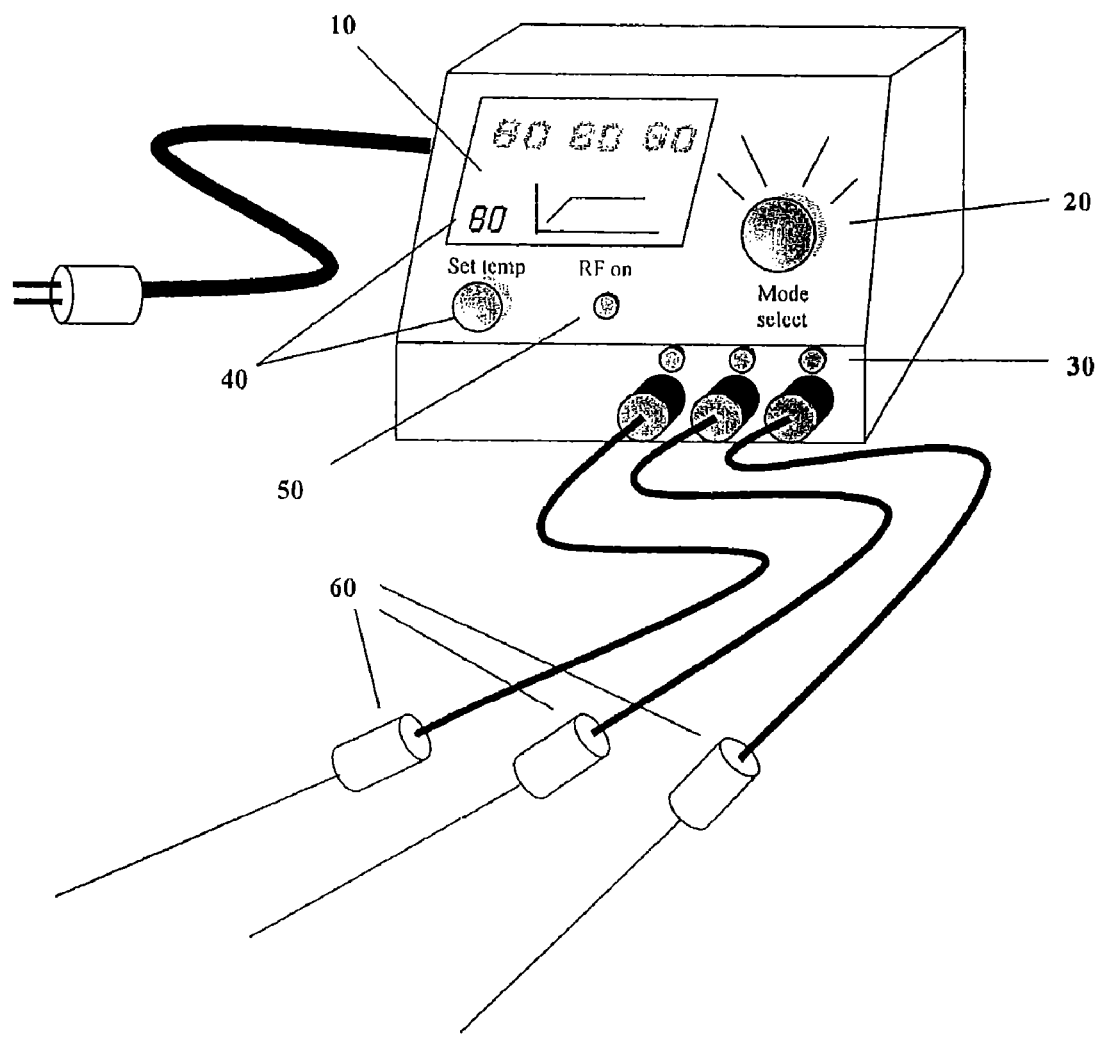
FIG. 1 represents a simple exemplary embodiment of the presently described system.

Referring to FIG. 1, an exemplary embodiment is illustrated. Mode select switch 20 allows the user to independently connect each electrode, each of which is identified as 60, to the high frequency power source. This permits the high frequency power source to selectively be connected to each electrode for the purpose of doing individual impedance measurements or stimulation threshold testing. An additional selection on the mode select switch allows therapeutic high frequency energy to be delivered to each electrode 60. The high frequency energy is delivered simultaneously to each electrode and the individual electrode temperatures are measured and continuously compared to the user set temperature, represented by 40 in FIG. 1. As also shown in FIG. 1, the electrodes are separate and not connected to one another. In other words, the electrodes are separate probes that each incorporate active electrode elements. The term "electrode(s)" as used alone hereinafter refers to a probe(s) having the active electrode element(s). In this embodiment the individual electrode temperatures are displayed on a two-dimensional graphics panel identified by 10 in the figure. Also within the graphics display is a representation of temperature vs. time displayed in graphic format. Indicator lights, represented by 30 in FIG. 1, indicate which electrode is active at that particular moment. In this way the user always knows which electrode is active when the mode select has been set to a particular electrode, and will also indicate during high frequency therapeutic treatment which electrodes are being activated at any given time.

It is very important to note two things from this figure—one is that to the high frequency power source that delivers the high frequency energy and/or low frequency stimulation pulses could be incorporated into this device or could be a separate stand-alone unit, with this device interposed between the high frequency power source and the electrodes. Though the figure shows this device as being AC line connected (that is requiring an electrical outlet for the unit to be plugged into), a battery-operated device may also be used.

It should also be understood that mode selection could be done in many ways and the features of this user interface could be achieved with or without displays, and could use up/down pushbuttons rather than rotatable selector knobs. For instance, mode select could individually connect each electrode to the high frequency device, and could also have a position which independently connected each electrode to any EMG measuring circuit, where the EMG signal was then displayed on a two-dimensional graphics display. An additional position on the mode select would be high frequency energy delivery where either continuous or pulsed high frequency energy was delivered simultaneously to each electrode and a feedback circuit was incorporated to maintain each electrode tip at a temperature equal to set temp.

It should also be noted there are many ergonomic manifestations of this invention and it would be possible to add additional displays, buttons, and/or indicators to allow and/or assist the operator in controlling the device. For instance, FIG. 1 has an RF on indicator light, represented by 50, which will indicate whenever high frequency energy is being delivered to the electrode outputs.

Figure 2:
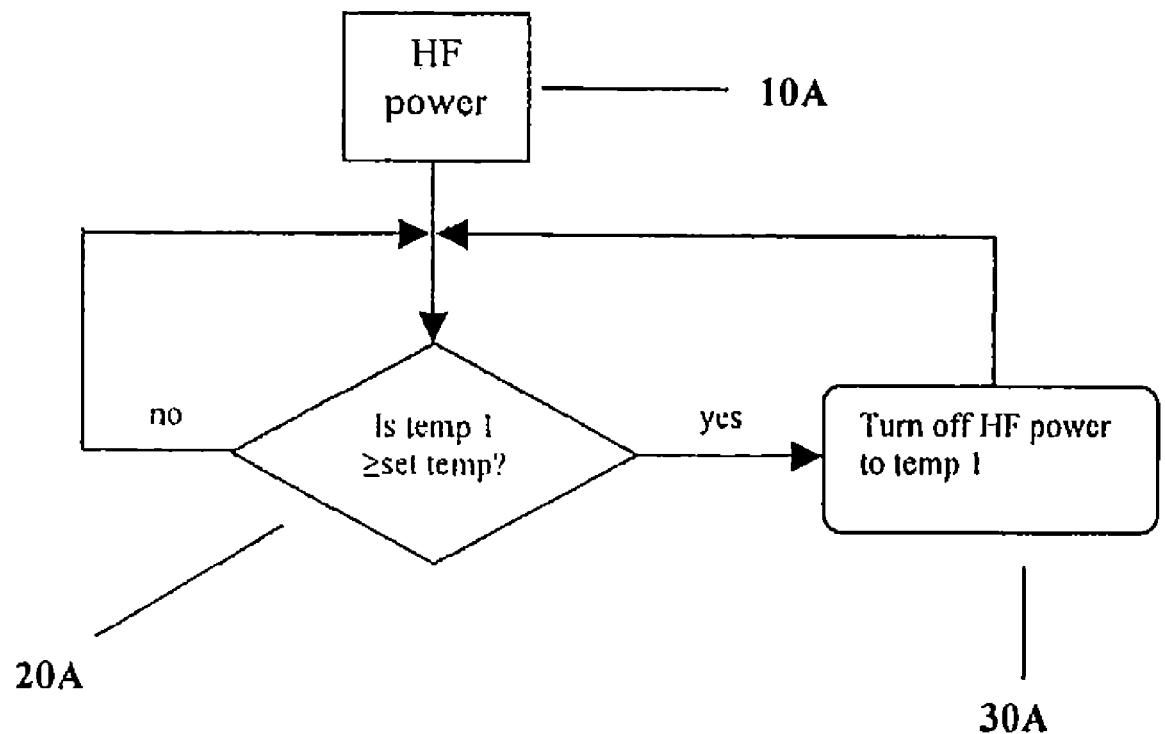
FIG. 2 illustrates an exemplary temperature feedback control mechanism.

FIG. 2 is a logic control diagram indicating a basic exemplary feedback mechanism for each of the temperature control electrodes. HF power, identified as 10A in the figure, is delivered system. The temperature of the electrode receiving this HF energy, as well as the user set temperature, is measured and a decision point is reached, represented by 20A in the figure. If the electrode temperature is greater than the user set temperature, the HF power is turned off to that electrode. This action is represented by block 30A in FIG. 2. Then this process starts all over again, where the electrode temperature is once again compared to the user set temperature. Conversely, if the measured temperature for that particular electrode is less than the user set temperature the HF remains on, and again, the electrode temperature is subsequently compared to the user set temperature. In this way temperature feedback is realized, which will maintain the electrode temperature at the same level as the user set temperature.

Figure 3:
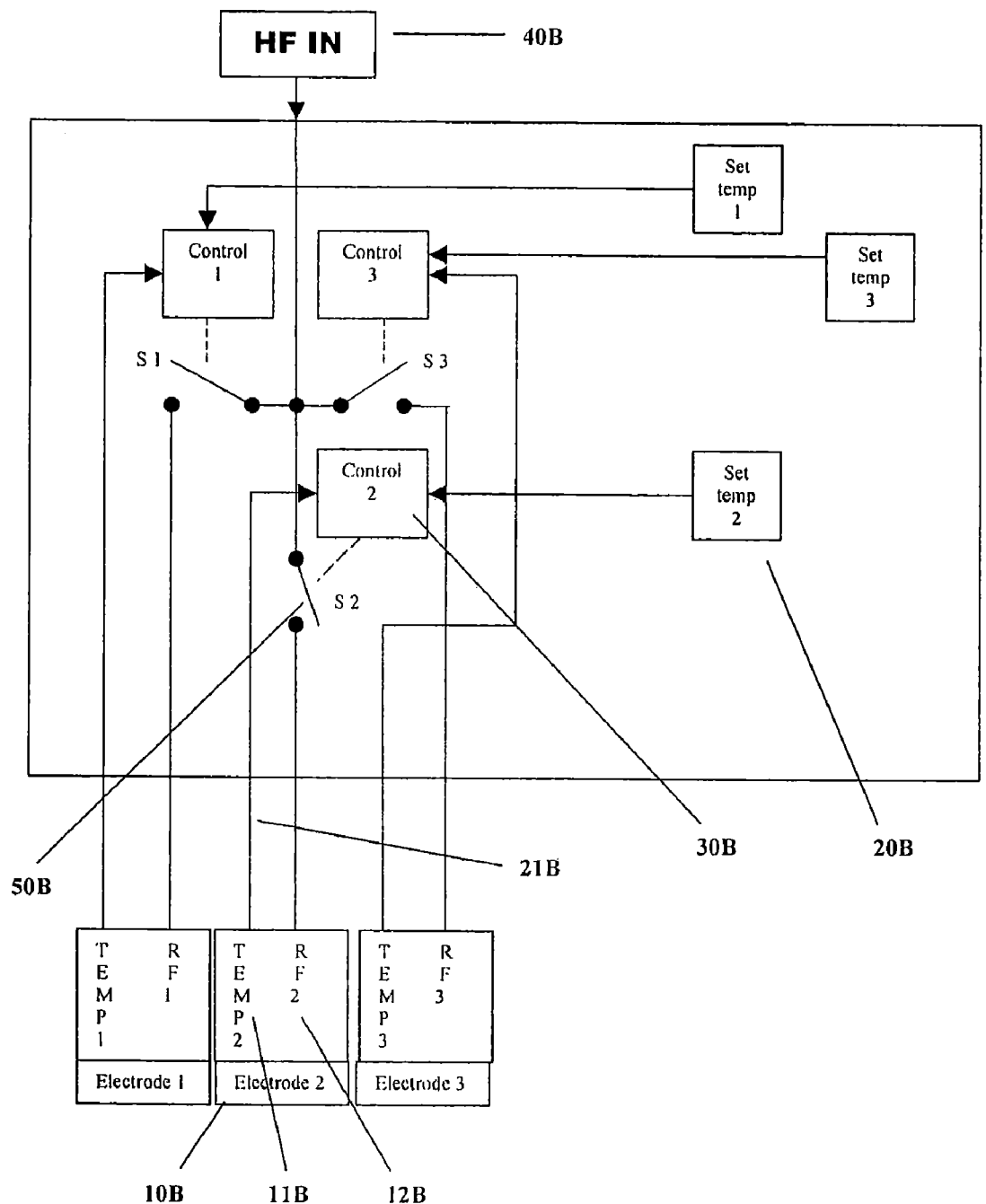
FIG. 3 is a schematic illustrating an exemplary setup for how the electrode set temperature is maintained.

FIG. 3 is a more detailed schematic of an exemplary feedback control mechanism. Note that this circuit is only representative of the HF energy delivery, and other connections have been omitted for clarity. As an illustration of how the circuit functions, Electrode 2 has been chosen as an example. However the same descriptions apply to Electrode 1 and Electrode 3, and in fact it should be emphasized that this embodiment permits temperature control of more than one electrode. In other words two, three, four, or more different electrodes can be controlled with this device.

10B in the figure represents Electrode 2. As can be seen by 11B, and 12B, a temperature sensor is incorporated into the electrode that reports the temperature at the electrode tip, as well as a means for applying the high frequency energy to the electrode. Temperature is reported via 21B to Control 2, identified by 30B in the figure. Control 2 also has an input identified as set temperature 20B, and compares these two signals to determine whether to open or close switch S2 (identified by 50B). It is important to note that S2 is a generic switch and can be achieved both electrically and/or mechanically and/or optically. The High Frequency energy in, represented by 40B in the figure, is therefore connected and disconnected to Electrode 2 via switch S2. As switch S2 is opening and closing via Control 2, (which is constantly comparing the user set temperature to the reported electrode tip temperature and determining whether to deliver HF energy to Electrode 2), a feedback circuit is established which will maintain the Electrode 2 temperature at the user set temperature.

Figure 4:
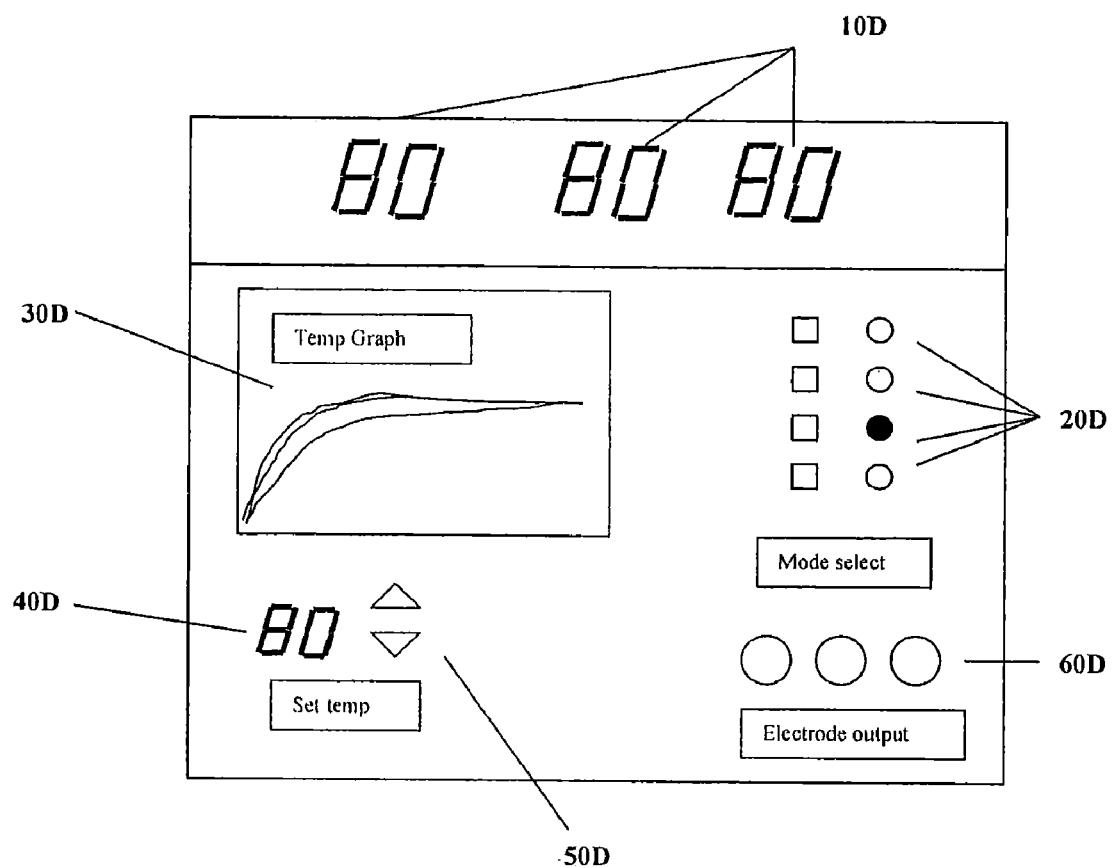
FIG. 4 is another exemplary embodiment showing the representation of the temperature of each of the electrodes in graphical form.

In FIG. 4, another exemplary embodiment of the user interface is illustrated. As identified by 10D and 40D, it is clear that electrode temperature and/or other pertinent parameters need not be displayed on a two-dimensional screen. These could be represented, for instance, by LED or LCD digits. 30D again represents a two-dimensional graphics display, in this case displaying temperature. Again, a graphics display is not necessary to realize the presently described system and method. To demonstrate exemplary options for user interface, the mode selector has been represented by a series of buttons that are associated with indicator lights identified as 20D in the figure and Set temp has been identified as up/down arrows as shown by 50D. The electrode outputs have been schematically represented by 60D.

Figure 5:
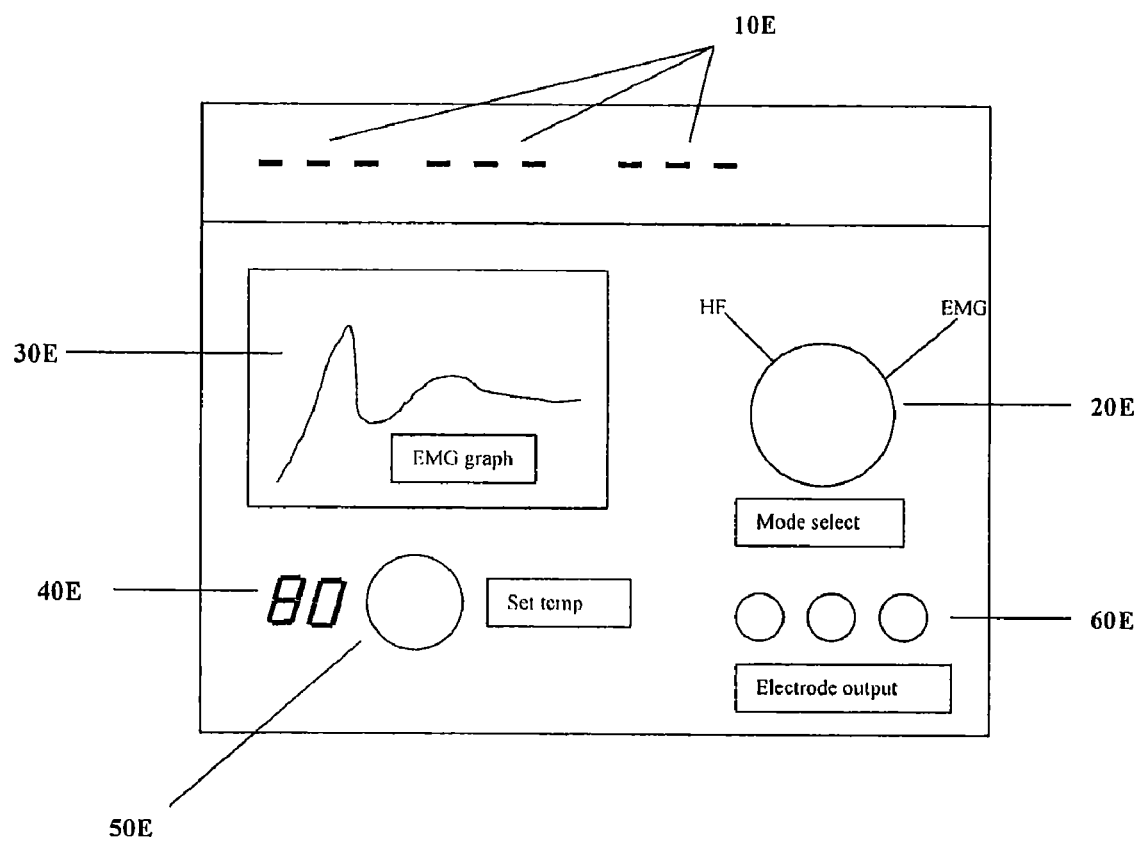
FIG. 5 is another exemplary embodiment which also illustrates the graphing of the EMG signal.

In FIG. 5, additional exemplary embodiments of the device are shown where, this time, the mode selector 20E has a position for EMG in addition to a high frequency energy delivery position. On the two-dimensional display, an EMG signal can be represented, thus identifying electrophysiological activity of a nerve before and/or after the high frequency treatment. For completeness, 60E identifies the electrode outputs, were once again three have been illustrated, although any number greater than 1 is possible with the present system and method. The Set temp user interface has been represented in this diagram as a knob 50E, though as mentioned earlier there are other contemplated ways to achieve this user interface. 40E identifies the actual set temperature. 10E is indicating that the temperature displays of the electrodes (--) is not relevant since they would indicate body temperature (37 C), though this temperature could be displayed if desired.

Figure 6:
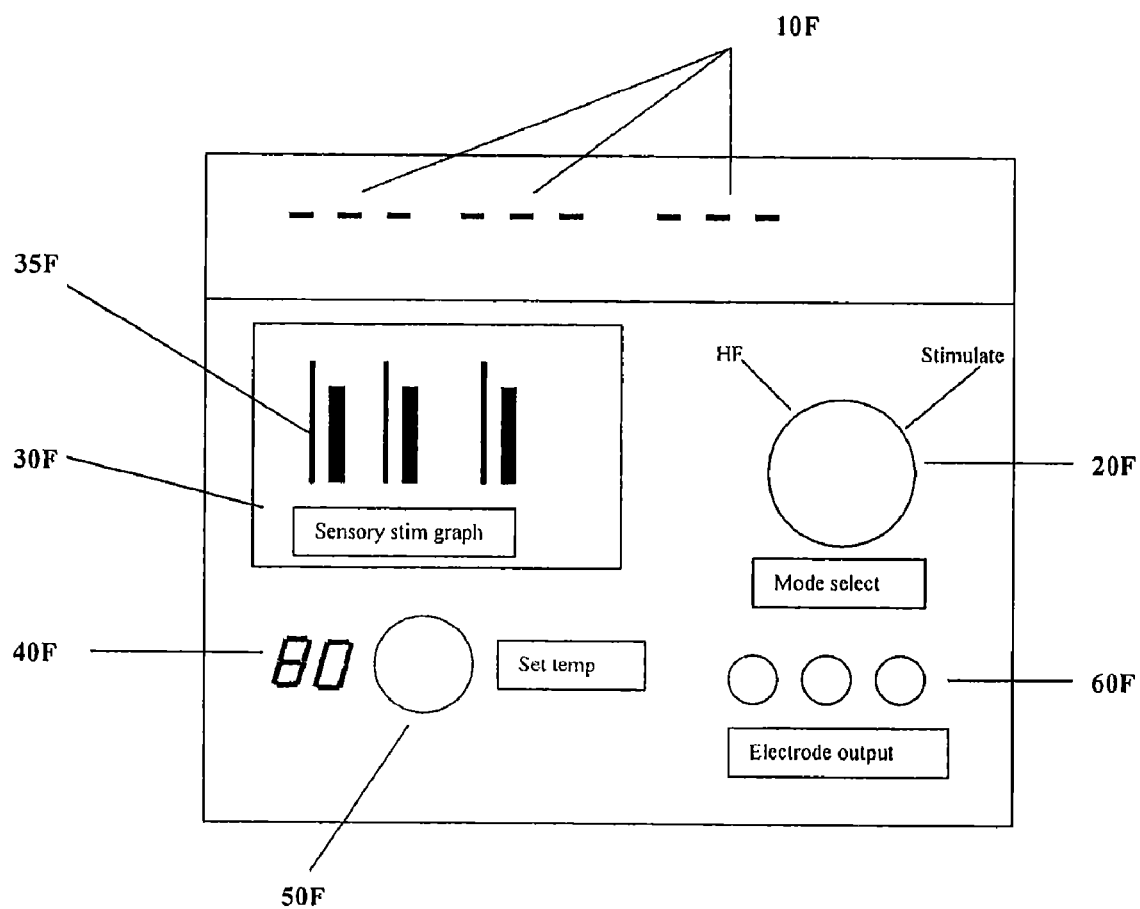
FIG. 6 is another exemplary embodiment showing one method of representing pre and post-treatment sensory stimulation thresholds.

FIG. 6 is an exemplary embodiment showing a sensory stimulation graph 30F, being displayed on the device. In this particular diagram, each electrode has associated with it a thin line and a fat line 35F indicating pre- and post-stimulation sensory thresholds for each electrode. Again, there are many contemplated ways that these parameters could be represented, and this is just an example of one of many ways in which to achieve a representation of these parameters that are identifiable to the user. The mode select switch, identified as 20F, has settings for both high frequency energy and stimulation. The dashes (--), indicated by 10F in the figure, represent temperature, which is irrelevant in this mode, since with no energy delivery there is no therapeutic heating and all of the electrodes will be reading body temperature (which could of course be displayed. The electrode outputs, represented by 60F, once again indicate three connections though any number of electrodes greater than one should be covered within the scope of this inventiois contemplated. Set temp is represented by 5F in the figure, and its associated value is represented by 40F in the figure and is depicted as a two digit display.

Figure 7:
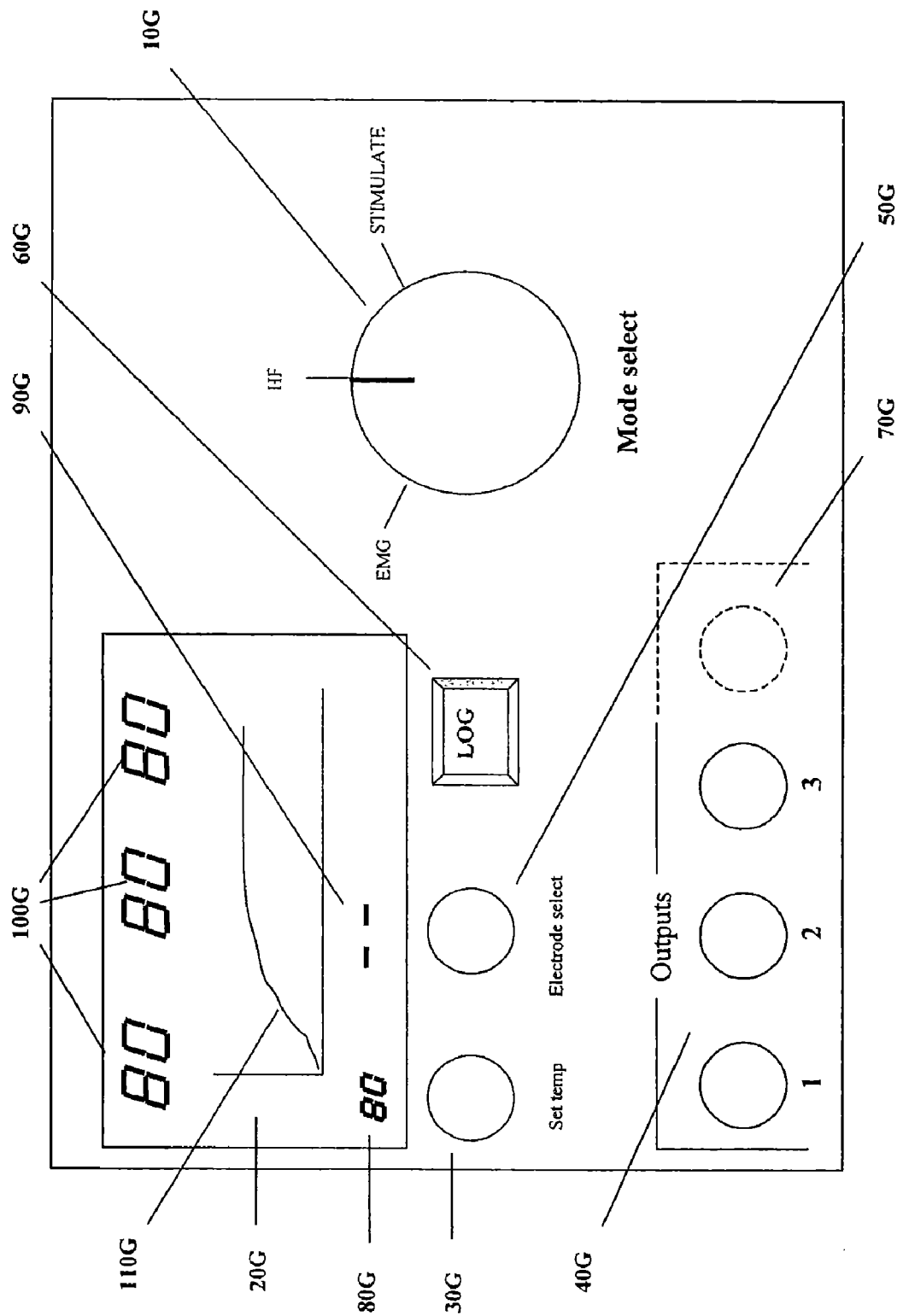
FIG. 7 is another exemplary embodiment showing three distinct mode selections, as well as an exemplary method for selecting each electrode individually and further an exemplary method to record sensory stimulation thresholds.

FIG. 7 is another exemplary embodiment. Illustrated is a mode select button, 10G, which allows the user to select between EMG, HF, and stimulate modes. When stimulate or EMG mode is selected, a digit(s) represented by 90G, indicates which electrode is selected, as in these modes it is important to select one electrode at time, and to know which electrode is selected. The electrode selection is made by the knob identified as 50G in the figure. In this particular embodiment, the user set temperature is identified as a knob indicated by 30G, and the set temperature value is represented by 80G in the figure, and is incorporated within a two-dimensional graphics display 20G. A time vs. temperature graph is indicated by 110G in the figure, and the individual electrode temperatures, if HF is selected on the mode select, is indicated by 100G in the figure. 40G once again indicates three outputs, and 70G represented by the dotted lines indicate that more than three electrodes, or less than three electrodes (as long as number of electrodes is greater than one), is contemplated. 60G identifies a log button. This button is used in stimulate mode, since the user must identify what stimulation voltage threshold is to be saved for future display.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A device for use in delivering therapeutic treatment to a plurality of nerve locations, the device comprising:
a radio frequency energy source having an RF output;
a plurality of electrode outputs operably coupled to the RF output, wherein each of the electrode outputs is separately and individually connectable through an electrical conductor to at least one of a plurality of probes;

a user interface for selecting a user-settable temperature associated with any of the electrode outputs; and feedback control circuitry to individually regulate energy delivery from the radio frequency energy source to each of the plurality of electrode outputs, so as to simultaneously maintain the user-settable temperature associated with each of the electrode outputs for electrode tips on probes connected to said electrode outputs.

2. The device of claim 1, further comprising a plurality of temperature sensor inputs, each of the plurality of temperature sensor inputs adapted to receive temperature information from at least one temperature sensor incorporated into at least one of the probes.

3. The device of claim 2, wherein the electrode outputs include the temperature sensor inputs.

4. The device of claim 2, further comprising a plurality of temperature displays corresponding to the plurality of temperature sensor inputs.

5. The device of claim 1, wherein the feedback control circuitry comprises a plurality of switches coupled between the RF output and the corresponding plurality of electrode outputs.

6. The device of claim 5, further comprising a plurality of sensor inputs adapted to receive temperature information from a plurality of temperature sensors at a corresponding plurality of electrodes tips.

7. The device of claim 1, wherein the feedback control circuitry comprises a plurality of feedback control circuits, each feedback control circuit corresponding to one of the plurality of electrode outputs.

8. The device of claim 7, further comprising a plurality of sensor inputs adapted to receive temperature information from a plurality of temperature sensors at a corresponding plurality of electrode tips.

9. The device of claim 1, further comprising a plurality of probes, each probe having an input, and one of the electrodes tips, wherein each probe input is coupled to the one of the electrode outputs.

10. The device of claim 9, wherein the probes are at least partially electrically insulated over at least part of a shaft of the probes.

11. The device of claim 9, wherein the plurality of probes are separate and not connected to one another.

12. The device of claim 1, further comprising a plurality of indicators corresponding to the plurality of electrode outputs, to indicate that a probe is receiving energy from the radio frequency energy source.

13. The device of claim 12, wherein the indicators comprise indicator lights.

14. The device of claim 1, further comprising a set temperature display to display the temperature set by the user.

15. The device of claim 14, wherein the user interface comprises a plurality of temperature controls, each temperature control corresponding to one of the plurality of electrode outputs.

16. The device of claim 14, further comprising a plurality of temperature sensor inputs, each of the plurality of temperature sensor inputs adapted to receive temperature information from a temperature sensor incorporated into one of the probes.

17. The device of claim 16 further comprising a plurality of individual electrode temperature displays corresponding to the plurality of temperature sensor inputs.

18. The device of claim 1, further comprising a graphics panel adapted to display at least one of the operating parameters of the device.

19. The device of claim 18, wherein the graphics panel is adapted to display the temperature of a plurality of electrode tips.

20. The device of claim 18, wherein the graphics panel is adapted to display both the temperature of a plurality of electrode tips, and the temperature of a plurality of electrode tips versus time.

21. The device of claim 1, wherein the RF output provides pulsed high frequency energy.

22. The device of claim 1, further comprising a reference electrode to provide a path for return current from two or more probes.

23. A system for use in delivering therapeutic treatment to a plurality of nerve locations, the system comprising:

a radio frequency energy source having an RF output;

a plurality of separate probes which are not connected to one another, each having a temperature sensor and an electrode tip, the temperature sensor arranged in the probes so as to provide information regarding temperature of an electrode tip;

a plurality of electrode outputs coupled to the RF output, wherein each of the electrode outputs is adapted to receive temperature information from and provide radio frequency energy to one of the probes; and feedback control circuitry to individually regulate energy delivery from the radio frequency energy source to each of the plurality of probes, so as to simultaneously maintain the temperature reported by the temperature sensor of each of the probes.

24. The system of claim 23, further comprising a plurality of temperature displays corresponding to the temperature information received at each of the electrode outputs.

25. The system of claim 23, further comprising a user interface for selecting a user-settable temperature individually associated with any of the electrode outputs.

26. The system of claim 23, wherein the feedback control circuitry comprises a plurality of feedback control circuits each corresponding to one of the plurality of electrode outputs.

27. The system of claim 23, further comprising a reference electrode to provide a path for return current from the plurality of probes.

* * * * *

UNITED STATES PATENT AND TRADEMARK OFFICE
Certificate

Patent No. 7,853,326 B2            Patented: December 14, 2010

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: William J. Rittman, III, Lynnfield, MA (US); and Howard Morgan Clarke, Hampshire (UK).

Signed and Sealed this Twenty-fifth Day of December 2012.

*NIKETA PATEL*
*Supervisory Patent Examiner*
Art Unit 3762
Technology Center 3700